United States Patent

Na et al.

[11] Patent Number: 6,162,955
[45] Date of Patent: Dec. 19, 2000

[54] MANUFACTURING METHOD FOR PERFLUOROETHANE

[75] Inventors: Doo-Chan Na; Ook-Jae Cho; Jae-Gug Ryu, all of Ulsan, Rep. of Korea

[73] Assignee: Ulsan Chemical Co., Ltd., Ulsan, Rep. of Korea

[21] Appl. No.: 09/591,852

[22] Filed: Jun. 12, 2000

[51] Int. Cl.[7] .................................................. C07C 19/08
[52] U.S. Cl. ............................................................. 570/123
[58] Field of Search ............................................ 570/123

[56] References Cited

U.S. PATENT DOCUMENTS

| | | | |
|---|---|---|---|
| 4,220,606 | 9/1980 | Moore | 570/123 |
| 5,302,764 | 4/1994 | Sekiya et al. | 570/123 |
| 5,406,008 | 4/1995 | Sievert | 570/123 |

Primary Examiner—Alan Siegel
Attorney, Agent, or Firm—Harrison & Egbert

[57] ABSTRACT

A method for producing a high purity of perfluoroethane from hydrofluoroethane ($C_2F_xH_y$, $1 \leq x$, $1 \leq y \leq 5$, $x+y=6$). Cobalt difluoride ($CoF_2$) as a catalyst is activated into cobalt trifluoride ($CoF_3$) as a result of the contact reaction with fluorine gas in a reactor. The reactor is purged by removing the fluorine gas remaining in the reactor. The remaining gas is allowed to react with sulfur to give sulfur hexafluoride ($SF_6$) which is then removed. The hydrofluoroethane is converted into perfluoroethane as a result of the catalyst of the activated cobalt trifluoride at 300–350° C. The feedstock is safer and less corrosive than triple bond-containing compounds such as acetylene. In the method of the present invention, the formation of $CF_4$ is extremely restrained and no inert gases are employed, so that a very high purity of $C_2F_6$ can be obtained at a high conversion rate.

2 Claims, No Drawings

MANUFACTURING METHOD FOR PERFLUOROETHANE

BACKGROUND OF THE INVENTION

1. Field of the Invention

The present invention relates to a method for producing perfluoroethane. More particularly, the present invention relates to a method for producing perfluoroethane from ethylenic hydrofluorocarbon in the presence of a cobalt catalyst. The term "ethylenic hydrofluorocarbon" as used herein means a fluoroethane containing 1–5 hydrogen atoms, represented by $C_2F_xH_y$, $1 \leq x$, $1 \leq y \leq 5$, $x+y=6$.

2. Description of the Related Art

Forming a gas phase at room temperature, perfluoroethane (hexafluoroethane) with a boiling point of −79 to −78.6° C. is a very useful industrial compound. For example, it is used as an etching gas for silicon wafers in the manufacture of semiconductors, a cleaning gas, an electrically insulating gas, a leak test gas, etc. In particular, this gaseous compound is required to be extremely low in its impurity content when used for the manufacture of semiconductor devices.

There are various known methods for manufacturing perfluoroethane, which are typically divided into five types as follows:

(1) Direct fluorination: ethane gas is directly reacted with fluorine gas ($F_2$);

(2) Electrochemical fluorination: ethane or ethylene is fluorinated under an electrolysis condition;

(3) Hydrofluorination: perhaloethane ($C_2F_xCl_y$) compounds are fluorinated in the presence of a catalyst;

(4) Pyrolytic fluorination: tetrafluoroethylene is fluorinated while being thermally decomposed with $CO_2$; and (5) compounds with triple bonds, such as acetylene, are reacted with metal fluoride, such as $CoF_3$, $MnF_3$, $AgF_2$, etc., for fluorination (Japanese Pat. Laid-Open Publication Nos. Heisei 3-167,141).

The direct fluorination in which the hydrogen atoms of ethane are directly replaced with fluorine gas ($F_2$) is conducted under extreme conditions showing a heat of reaction at 102–104 kcal/mole, so that cleavage occurs at the C—C bond as well as the C—H bonds, producing a large quantity of $CF_4$. In order to reduce the C—C bond cleavage, fluorine gas is diluted with an inert gas such as nitrogen gas before participation in the fluorination. Such an inert gas certainly alleviates the cleaving of the intercarboneous bond, but causes a significant problem particularly when the perfluoroethane gas is used in the fabrication of semiconductor devices because it may act as an impurity. In addition, low boiling point compounds like perfluoroethane (Bp: −79 to −78.6° C.) have difficulty separating from nitrogen gas, causing significant loss upon the purification. Further, the direct feeding of fluorine gas requires a reactor of a special structure, which gives rise to corrosion in the apparatus, and produces difficulty in temperature control on account of an explosive reaction. Therefore, the direct fluorination is disadvantageous in its application for the commercialization of the production of such a low boiling point compounds. On the other hand, it is recommended to be applied for the production of such compound that are relatively high in boiling point with large molecular weights because they can be easily separable from the inert gas.

In accordance with the electrochemical fluorination, ethane is fed below a specially constructed carbon electrode in a fluorine gas-electrolyzing bath to react to the fluorine gas, which is generated along the surface of the carbon electrode. This method, however, produces a large quantity of by-products like the direct fluorination. In addition, because the electrochemical fluorination occurs on the surface of the electrode, the feedstock cannot help being provided at a limited amount in connection to the limited length of the electrode. So, the electrochemical fluorination suffers from a significant problem of being poor in production yield.

As for the hydrofluorination, it is mainly applied for the reaction of perhaloethanes such as trichlorotrifluoroethane (CFC-113), dichloro trifluoroethane (CFC-114) and chloropentafluoroethane (CFC-115) with hydrogen fluoride in the presence of a catalyst. For this catalytic reaction, Cr or Al catalysts are used at high temperatures under high pressures. In the perhaloethane, e.g., $C_2F_5Cl$, just before complete fluorination, the bond between the carbon and the last chlorine atom is very strong owing to the influence (electronegativity) of adjacent fluorine atoms, so that the chlorine atom is very difficult to replace with a fluorine atom. In other words, the hydrofluorination shows low conversion rates into perfluoroethane. High temperatures and high pressures are thus needed to overcome such low conversion rates, but require a high cost of equipment.

When perfluoroethane is prepared from tetrafluoroethylene, this reactant is directly reacted with fluorine gas or thermally decomposed by use of $CO_2$. The direct reaction of $C_2F_4$ with $F_2$ gas is very volatile, producing a large quantity of $CF_4$, like the above direct fluorination. The preparation of perfluoroethane through the thermal decomposition reaction between $C_2F_4$ and $CO_2$ demands high temperatures of greater than 700° C. and is problematic in that the restraint of $CF_4$ production must rely on temperature control.

Japanese Pat. Laid-Open Publication No. Heisei 3-167141 uses compounds with intramolecular triple bonds, such as acetylene, methylacetylene, 2-butyne, methylethylacetylene, etc, as materials for preparation of perfluoroethane, disclosing that such a triple bond compound is converted into perfluoroethane in the presence of a $CoF_3$ catalyst with a minimum of C—C bond cleavage. ($CF_4$ production 0.2%) based on the following reaction formulas:

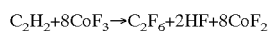

$C_2H_2 + 8CoF_3 \rightarrow C_2F_6 + 2HF + 8CoF_2$

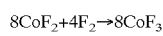

$8CoF_2 + 4F_2 \rightarrow 8CoF_3$

The patent lays emphasis on the high selectivity for perfluoroethane (97% or greater), reporting the loss of two HF equivalents only. However, a significant disadvantage of this reaction is the extreme preponderance of the catalyst over the reactant used. For instance, the amount of the reactant which can be fed in the reaction is merely 5% of that of the catalyst fed (catalyst 55 kg, reactant 800 ml/min, reaction period 2 hrs). The reason is that 8 moles of CoF3 are consumed per mole of $C_2H_2$ as shown in the above reaction formulas. Where the feedstock $C_2H_2$ is used greater than 5% of the amount of the catalyst, it is virtually impossible for all of the feedstock to advance to the final product $C_2F_6$ and it seems to produce a large quantity of the intermediate product. This coincides with the disclosure of another document (Russia Journal of Organic Chemistry Vol. 30, No. 8 (1994)). A plant which utilizes this reaction would have a reactor whose size is exceptionally large. Thus, the method has disadvantages of being economically unfavorable and poor in conversion rate.

The fluorination of triple bond-containing compounds such as acetylene into perfluoroethane can be easily achieved. But the feedstock is expensive and also dangerous requiring careful treatment.

BRIEF SUMMARY OF THE INVENTION

Therefore, it is an object of the present invention to overcome the above problems encountered in prior arts and to provide a novel method for manufacturing perfluoroethane from hydrofluoroethane, which is effectively preventive of the production of $CF_4$, a by-product causing a decrease of $C_2F_6$ purity because of the difficulty in separating them from each other.

It is another object of the present invention to provide a novel method for the conversion of hydrofluoroethane into perfluoroethane, in which the cleavage of the C—C bond hardly occurs, thereby improving the conversion rate.

And also, we aim to manufacture perfluoroethane from hydrofluoroethane, in which only a small amount of fluorine gas is consumed so as to obtain an economical advantage.

A further object of the present invention is to provide a novel method for manufacturing perfluoroethane from hydrofluoroethane, in which reactions are conducted in the absence of inert gas thereby preventing the purity decrease due to the use of inert gas.

BRIEF DESCRIPTION OF THE SEVERAL VIEWS OF THE DRAWINGS

The above and other objects, features and other advantages of the present invention will be more clearly understood from the following detailed description taken in conjunction with the accompanying drawing FIG. 1 is a schematic process view showing the production of perfluoroethane according to the present invention.

DETAILED DESCRIPTION OF THE INVENTION

The present invention pertains to the preparation of perfluoroethane from hydrofluoroethanes with 1–5 intramolecular hydrogen atoms, ($C_2F_xH_y$, wherein $1 \leq x$, $1 \leq y \leq 5$, x+y=6), especially, 1,1,1-trifluoro 2,2-difluoroethane ($CF_3CHF_2$, hereinafter referred to as "HFC-125"), 1,1,1-trifluoro 2-fluoroethane ($CF_3CH_2F$, hereinafter referred to as "HFC-134a"), and 1,1,1-trifluoroethane ($CF_3CH_3$, hereinafter referred to as "HFC-143a") in the presence of a cobalt catalyst ($CoF_3$).

Hydrofluoro carbon (hereinafter referred to as "HFC") compounds have recently attracted intense attention for their ability to substitute for chlorofluoro carbon (hereinafter referred to as "CFC"). In fact, they are widely used as a coolant in automobiles, refrigerators, air conditioners, etc., without producing harmful effects. Since the revelation of the CFC's action of destroying the ozonosphere, extensive and intensive research has been directed to the development of its substitutes and HFC compounds, such as HFC-134a, were found to be suitable ones. Their production on a commercial scale was also successfully achieved. Therefore, HFC compounds are abundant and can be obtained at relatively low prices. Thus far, however, there have not been developed methods of preparing $C_2F_6$ from HFC compounds.

When HFC-125 is used as a substrate to produce $C_2F_6$ with the aid of $CoF_3$, the reaction conforms to the following reaction formula:

$$CHF_2CF_3 + 2CoF_3 \rightarrow CF_3CF_3 + HF + 2CoF_2$$

$$2CoF_2 + F_2 \rightarrow 2CoF_3$$

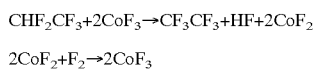

In order to produce 1 mole of $C_2F_6$, as shown in the reaction formula, 1 mole of HFC-125 and 1 mole of fluorine gas are consumed under the catalytic action of 2 moles of $CoF_3$ with a side production of 1 mole of hydrogen fluoride. In the course of producing $C_2F_6$ from HFC-125 in accordance with the present invention, only a portion of the starting material remains unreacted. The portion of the unreacted HFC-125 can be largely reduced by controlling the equivalents of the catalyst, so that perfluoroethane is obtained with a high purity.

When using HFC-134a as a substrate for the catalyst of $CoF_3$, the production of $C_2F_6$ conforms to the following reaction formula:

$$CH_2FCF_3 + 4CoF_3 \rightarrow CF_3CF_3 + 2HF + 4CoF_2$$

$$4CoF_2 + 2F_2 \rightarrow 4CoF_3$$

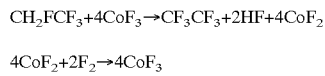

As seen in the reaction formula, 4 moles of $CoF_3$ are used per mole of HFC-134a to produce 1 mole of $C_2F_6$ along with 2 moles of hydrogen fluoride. In this case, the starting material HFC-134a and the primary fluorination product HFC-125 which is produced in this process, may remain partially unreacted at a shortage of the catalyst. However, the unreacted compounds can be reduced to a minimal level by controlling the mole numbers of the catalyst, so that perfluoroethane is obtained with a high purity.

When the catalytic preparation of perfluoroethane is initiated from HFC-143a, its reaction formula is as follows:

$$CH_3CF_3 + 6CoF_3 \rightarrow CF_3CF_3 + 3HF + 6CoF_2$$

$$6CoF_2 + 3F_2 \rightarrow 6CoF_3$$

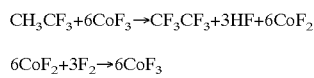

As seen in the reaction formula, 6 moles of $CoF_3$ are used per mole of HFC-143a to produce 1 mole of $C_2F_6$ along with 3 moles of hydrogen fluoride. In this case, the starting material, HFC-143a, HFC-134a, and HFC-125 which are produced in this process, may remain partially unreacted because of a shortage of the catalyst. However, these unreacted compounds can be reduced to minimal levels by controlling the mole numbers of the catalyst, so that perfluoroethane is obtained with a high purity.

The present invention, as indicated in the above reaction formulas, comprises two processes: the catalyst is activated at 250–300° C. with fluorine gas for the conversion into $CoF_3$, and HFC is supplied to the activated catalyst at 350–400° C. to produce perfluoroethane. To achieve commercialization, the catalyst activation process and the production reaction process must be continuously conducted in an alternative pattern. To this end, two 30 liter reactors were used for the continuous production of perfluoroethane, in the present invention. However, it should be noted that the number of the reactors is not limitative of, but descriptive of the present invention.

A description will be given of the processes of the present invention in conjunction with the production. facility shown in FIG. 1.

Catalyst Activation Process

In the production facility of FIG. 1, valves 2, 3, 4 and 6 are closed while a valve 1 is open so as to feed $F_2$ gas from a fluorine gas cylinder to a reactor 8 of a horizontal type.

Because of the fine powder phase of $CoF_2$, this catalyst is charged at an amount of 50–60% of the volume of the reactor 8 in order to allow fluorine gas and feedstock to smoothly flow. Within the reactor 8, a stirring paddle is positioned, and rotated at 20 rpm during the implementation of the catalyst activation and production reaction process. In two reactors A and B (only one reactor is shown in FIG. 1), 11 kg of the catalyst is charged respectively. In the reactor A, the temperature is raised to 250° C. to start the activation of the catalyst. While the production reaction is conducted in the reactor B, the catalyst activation is carried out with a supply of fluorine gas in the reactor A. In this regard, a sufficiently large amount of the fluorine gas is fed such that the catalyst activation is completed within a time period shorter by 50–60% than that of the production reaction. The reason is that, owing to the difference in temperature between the production reaction and the catalyst activation, it takes a significant amount of time for the temperature to increase from a point suitable for the catalyst activation to a point suitable for the production reaction and also to decrease vice versa. When the temperature control is accurately achieved, a continuous operation is possible.

Removal Process of Fluorine Gas Remaining in Reactor

After completion of the catalyst activation, the reactor temperature is elevated for the reaction of the feedstock. At this time, the fluorine gas may remain unreacted within the reactor. This remaining fluorine gas must be removed. If not, it reacts vigorously with the feedstock to cleave the C—C bond, producing $CF_4$ the existence of which deteriorates the product purity. After completion of the reaction, fluorine gas must be prevented from being leaked to the outside because it is toxic.

Feeding an inert gas in combination with raising the temperature enables the easy sweeping of the remaining fluorine gas, but the inert gas is apt to be contained as an impurity in the final product perfluoroethane, resulting in a deterioration in purity.

Alternatively, it may be suggested that a vacuum is applied to an outlet of the reactor to remove the inert gas. However, the fine powder phase of the catalyst makes it impossible to apply a strong vacuum necessary to completely remove the inert gas. Under such a strong vacuum, the fine powder of the catalyst as well as the inert gas is run out of the reactor together with the inert gas, clogging pipes, valves and the vacuum pump due to its piling up. In addition, this is economically unfavorable due to a loss of the catalyst. Further, even when the inert gas is sufficiently removed, if only a trace of fluorine gas exists, the vacuum pump remains under the high risk of corrosion.

In the present invention, an $SF_6$ reactor 11 charged with sulfur(S) is provided to an outlet of the production facility to convert the remaining, highly reactive fluorine gas into inert $SF_6$ through the reaction with sulfur. To the rear of the $SF_6$ reactor is provided an aspirator in which a low rough vacuum is applied with the aid of a vacuum pump 12 to remove the $SF_6$. As a result, the fluorine gas remaining in the reactor 8 is introduced into the $SF_6$ reactor by the vacuum pump 12 and converted into $SF_6$ which is then discharged to the outside by means of the aspirator.

Reaction Process of Cobalt Catalyst with HFC-125, HFC-134a and HFC-143a

After completion of the cobalt catalyst activation, the reactor is further heated to 350–400° C., followed by passing the HFC-134a at a flow rate of 600–800 ml/min through the reactor. HFC-125 and HFC-143a are allowed to flow at rates of 800–1000 ml/min and 400–600 ml/min, respectively. The products effluent from the reactor are subjected to alkali washing, pressurized to 2 kg/cm$^2$, passed through a molecular sieve to remove moisture, and re-pressurized to 15 kg/cm$^2$ for storage. The effluents which are taken at regular time period intervals are analyzed by gas chromatography. The gas chromatography results show that perfluoroethane can be produced from HFC-134a with a selectivity of as high as 99.7% at 350° C. when the reactant is allowed to flow at a rate of 600–800 ml/min, in accordance with the present invention. Far superior to that of ethylene or acetylene, such a high selectivity is attributed to the small number of the hydrogen atoms to be replaced, that is, as small as two hydrogen atoms of HFC-134a. Thus, because the loss of the fed fluorine gas into the by-product hydrogen can be reduced, a reduction is also brought about in the consumed amount of the fluorine gas. From HFC-125, perfluoroethane can be obtained with a selectivity of as high as 99.9% when it is reacted at 350° C. at a flow rate of 800–1,000 ml/min, in accordance with the present invention. This extremely high selectivity results from the existence of only one hydrogen atom to be replaced. However, this starting material is more disadvantageous in cost than HFC-134a. The method of the present invention is also found to be able to produce perfluoroethane from HFC-143a with a selectivity of 99.5% or higher at a reaction temperature of 350° C. at a flow rate of 400–500 ml/min.

Removal Process of Unreacted Materials

After completion of the production reaction, the reactor temperature should be decreased from 350–450° C. down to 250° C. in order to re-activate the catalyst whose activity has been exhausted. At this time, unreacted materials exist within the reactor. The unreacted materials, if not removed, react directly with fluorine gas in the next round of the catalyst activation to produce $CF_4$ as a result of the cleavage of the C—C bond, negatively affecting the purity of the final product.

In the present invention, after completion of the production reaction, the activation of the catalyst is accomplished by decreasing the temperature to 250° C., removing the remaining materials at a low rough vacuum, and passing fluorine gas through the reactor. Although a trace of inert gas exists in the reactor, it is sufficiently removed by influent fluorine gas and nearly all impurities are allowed to exit within the reaction system by the action of the aspirator provided to the rear of the $SF_6$ reactor.

Thus, in accordance with the present invention, perfluoroethane can be produced at high selectivity from HFC compounds, including HFC-125 ($CF_3CHF_2$), HFC-134a ($CF_3CH_2F$) and HFC-143a ($CF_3CH_3$) while fluorine gas is consumed at a minimal amount with a minimum of the loss into hydrogen fluoride. In addition, the method of the present invention employs the cobalt catalyst $CoF_2$ so as to improve the reaction conversion rate and clears unreacted materials by use of the fluorine gas to restrain the cleavage of the intercarboneous bond within the starting materials, so as to prevent the formation of $CF_4$ which is hard to separate from the final product. Together with the absence of $CF_4$, the use of fluorine gas, instead of inert gas, for the removal of unreacted materials gives a great contribution to the improvement of the purity of the desired product.

A better understanding of the present invention may be obtained in light of the following examples which are set forth to illustrate, but are not to be construed to limit the present invention.

EXAMPLE 1

11 kg of the catalyst $CoF_2$ was charged in each of two 30 liter reactors (15 cm×179 cm) which were then heated to 250° C., followed by feeding fluorine gas into one (A) of the two reactors to activate the catalyst (CoF$_2$ to CoF$_3$). The outlet of the reactor was directed to an SF$_6$ reactor (maintained at a reaction temperature of 120° C.) to prevent the direct leakage of fluorine gas into the air. After completion of the catalyst activation, the temperature of the reactor is elevated while a low pressure of vacuum is applied to the outlet of the SF$_6$ reactor.

When the reactor A was ready to implement the reaction procedure, a feedstock was fed to the reactor to induce the reaction while fluorine gas was fed to the other reactor (B) to conduct a new round of the catalyst activation. These two reactors were alternatively operated so as to continuously produce the desired product.

The reactor whose catalyst had been activated was heated to 350° C. and provided with HFC-134a at a flow rate of 617 ml/min. Products thus obtained were treated with 20% KOH in a scrubber 13 to remove hydrogen fluoride, then pressurized to 2 kg/cm in a primary compressor and then passed through a molecular sieve tower to remove moisture, after which the demoisturized products were re-pressurized to 15 kg/cm$^2$ for storage with the aid of a secondary compressor. Every eight hours, the reactors were alternatively operated so as to continuously produce the product. After 25 days of the continuous operation, 135 kg of C$_2$F$_6$ was produced. Quantitative analysis showed that the product had the average composition as follows:

CF$_4$: 0.02% or less
C$_2$F$_6$: 99.70% or greater
CF$_3$CHF$_2$: 0.18%
Others: 0.1% or less As shown, the formation of CF$_4$ was almost restrained to the content of 0.02% or less. After completion of the conversion reaction and the decrease of reaction temperature to 250° C., the reactor was purged by removing the remaining materials at a low rough vacuum, so as to prevent the production of the by-product CF$_4$. In addition, after the catalyst activation, the fluorine gas remaining within the reactor was swept out at a vacuum of 20 mmHg.

EXAMPLE 2

In the reaction system of Example 1, HFC-125, instead of HFC-134a, was fed at a flow rate of 830 ml/min. The fluorination results are as follows:

CF$_4$: trace
C$_2$F$_6$: 99.9% or greater
Others: 0.1% or less

As analyzed quantitatively, almost no CF$_4$ was formed while the feedstock HFC-125 was almost completely converted into perfluoroethane.

EXAMPLE 3

In the reaction system of Example 1, HFC-143a, instead of HFC-134a, was fed at a flow rate of 420 ml/min. The fluorination results are as follow:

CF$_4$: 0.02% or less
C$_2$F$_6$: 99.50% or greater
CF$_3$CHF$_2$: 0.33%
Others: 0.1% or less As analyzed quantitatively, the disadvantage in that the hydrogen atoms of HFC-143a outnumber those of HFC-134a by one, was overcome by feeding the feedstock at a lower flow rate than that of HFC-134a.

COMPARATIVE EXAMPLE 1

The same procedure as in Example 1 was repeated except that the conversion reaction was conducted at 300° C.

The final product was analyzed to have the following composition:

CF$_4$: 0.02% or less
C$_2$F$_6$: 88.40%
CF$_3$CHF$_2$: 9.73%
Others: 1.85%

Because the reaction condition were mild, the conversion of the feedstock into C$_2$F$_6$ was relatively poor while the amount of HFC-125 was increased.

COMPARATIVE EXAMPLE 2

The same procedure as in Example 1 was repeated except that the conversion reaction was conducted at 450° C.

The final product was analyzed to have the following composition:

CF$_4$: 5.55%
C$_2$F$_6$: 94.4%
CF$_3$CHF$_2$: 0.05%

At the extreme reaction condition, the C—C bond of the starting material was readily cleaved to increase the amount of CF$_4$.

As described hereinbefore, the present invention provides a method for producing a high purity of perfluoroethane from the feedstock safer and less corrosive than triple bond-containing compounds such as acetylene, at high conversion rates. In the method of the present invention, the formation of CF$_4$ is extremely restrained and no inert gases are employed, so that a very high purity of C$_2$F$_6$ can be obtained.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

We claim:

1. A method for producing perfluoroethane, comprising the steps of:

activating cobalt difluoride (CoF$_2$) into cobalt trifluoride (CoF$_3$) by the contact reaction with fluorine gas in a reactor;

removing the remnant fluorine gas from the reactor by reacting said fluorine gas with sulfur to give sulfur hexafluoride (SF$_6$) and drawing out the sulfur hexafluoride;

converting hydrofluoroethane into perfluoroethane by the contact reaction with the activated cobalt trifluoride at 300–350° C., said hydrofluoroethane being represented by the following chemical formula:

$$C_2F_xH_y$$

wherein $1 \leq x$, $1 \leq y \leq 5$, $x+y=6$.

2. A method as set forth in claim 1, where said hydrofluoroethane is selected from the group consisting of 1,1,1-trifluoro 2,2-difluoroethane, 1,1,1-trifluoro 2-fluoroethane and 1,1,1-trifluoroethane.

* * * * *